United States Patent [19]

Souppe et al.

[11] Patent Number: 4,751,325

[45] Date of Patent: Jun. 14, 1988

[54] PROCESS FOR THE PURIFICATION OF CARNITINE

[75] Inventors: Jérôme Souppe, Pau; Gisèle Haurat, Arthez-De-Bearne; Philippe Goulas, Pau, all of France

[73] Assignee: Societe Nationale Elf Aquitaine, France

[21] Appl. No.: 34,387

[22] Filed: Apr. 2, 1987

[30] Foreign Application Priority Data

Apr. 4, 1986 [FR] France ................. 86 04832

[51] Int. Cl.$^4$ .......................... C07C 99/12
[52] U.S. Cl. ................... 562/554; 562/567; 260/501.13
[58] Field of Search .............. 562/554, 567; 260/501.13

[56] References Cited

U.S. PATENT DOCUMENTS 4,221,869 9/1980 Vandecusteele ............... 435/117
4,602,039 7/1986 Cavazza ..................... 260/501.13

*Primary Examiner*—Michael L. Shippen
*Attorney, Agent, or Firm*—Ostrolenk, Faber, Gerb & Soffen

[57] ABSTRACT

Process of purification of carnitine, in which the aqueous medium containing the carnitine is first acidified, in order to cause the proteins present to precipitate, and, after their separation, the water of the medium is replaced by a lower alcohol which dissolves carnitine, at least hot, while the mineral substances separate out.

12 Claims, No Drawings

PROCESS FOR THE PURIFICATION OF CARNITINE

The invention relates to a new process for the purification of carnitine, namely 4-trimethylamino, -3-hydroxybutyric acid, and in particular L-carnitine obtained by biochemical means.

Carnitine is principally employed for biological applications, particularly pharmacalogical, cosmetic and dietary, so that its purity is an important condition of its use. Also, as chemical methods for its preparation lead to racemic mixtures, while only the L-stereo-isomer is biologically active, it is the biochemical process of preparation which is of interest because it provides the L-isomer. It is thus important to devise a process of purification allowing ready elimination of the impurities which are derived from the materials utilised in the biochemical process, in particular various proteins and mineral substances. It is this advantage which is of interest in connection with the process according to the invention; it allows avoidance of the standard chromatographic method which does not eliminate the mineral compounds.

The new process according to the invention makes possible the direct preparation of carnitine in its amphoteric form in place of a strong acid salt, in particular the hydrochloride, as is the case in the prior art, for instance as in French Pat. No. 2398046. On the other hand, it only comprises five stages at the most, while there are at least ten successive operations in the known process, using an ion exchange resin column.

The process of purification according to the invention is characterised in that the aqueous medium containing the carnitine is first acidified, in order to cause precipitation of the proteins present and, after their separation, the water of the medium is replaced by a lower alcohol which dissolves carnitine at least in the hot, while the mineral substances separate out. An alcoholic solution rich in the carnitine salt of good purity is so obtained.

When an even purer product is desired and in particular when production of the amphoteric compound

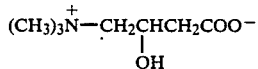

per se and not its salt is desired, the purification is completed in the following manner. The solid extracted from the above-mentioned alcoholic solution is taken up in aqueous solution, which is neutralised with a base to a pH of about 7.2 and the neutralised solution is treated so that the water becomes replaced by a lower alcohol, which causes precipitation of the salt of the base used for neutralisation of the acid which has served for acidification of the initial medium. The alcoholic solution remaining contains amphoteric carnitine of excellent purity, which can be recovered in the solid state, particularly by crystallisation in the cold, by drying the solution or by precipitation by the addition of a non-solvent liquid.

There follows in more detail the five stages of the process according to the invention, which is capable of providing a very pure L-carnitine from an impure aqueous solution of this compound, derived in particular from the medium obtained by the biological conversion of 3-dehydro-carnitine.

1—ACIDIFICATION OF THE MEDIUM

An acid, preferably strong, is added to the aqueous solution in order to lower its pH to a value of about 1 to 3, preferably around or equal to 2. Acids such as sulphuric, sulphurous, phosphoric, perchloric, benzenesulphonic etc. can be employed, $H_2SO_4$ being particularly suitable. This operation has the effect of precipitating the proteins which are found in the medium treated and which can thus be eliminated by filtration or centrifugation of the acidified liquid.

2—PRECIPITATION OF THE MINERAL SALTS

The filtrate derived from the preceding operation is treated so as to replace its water with a lower alcohol capable of dissolving carnitine. This can be effected by evaporation of the water of the solution and addition of the alcohol or by evaporation with entrainment of the alcohol. At the end, the alcoholic solution is maintained at the temperature at which the carnitine is wholly dissolved, while the mineral compounds precipitate and these are separated. The alcohol can be such as methanol, ethanol, methoxyethanol, isopropanol, n-propanol, n-butanol, tert.-butanol or isobutanol, ethanol being particularly appropriate. Mixtures of alcohols can be employed. Depending on the nature of the alcohol and the solubility of the carnitine, operation takes place at an appropriate temperature which in general is from 20° to 100° C.

3—RETURN TO AQUEOUS SOLUTION

From the alcoholic solution obtained in the preceding stage 2, the dissolved carnitine can be recovered in the form of a salt of the acid employed in stage 1, in a state of good purity. But if it is desired to take the purification to a further stage, where production of amphoteric carnitine in place of its salt is desired, the procedure is as follows. The carnitine salt is extracted from the alcoholic solution, particularly by evaporation of the alcohol or by precipitation by means of a non-solvent, such as a ketone for example. The latter means contributes further to improve the purity. This salt is dissolved in water, preferably at the rate of 100 to 500 g/l and the solution is subjected to the following stage 4°.

4—NEUTRALISATION

The solution derived from the preceding stage 3 is neutralised by the addition of a base, preferably caustic soda. While the pH at the end of the neutralisation can range between 6.9 and 7.4, it is preferably very close to or equal to 7.2. This neutralisation frees amphoteric carnitine according to the reaction:

$$HSO_4^-.(CH_3)_3\overset{+}{N}CH_2\underset{OH}{CH}CH_2COOH + 2Na.\overset{+}{O}\overset{-}{H} \longrightarrow$$

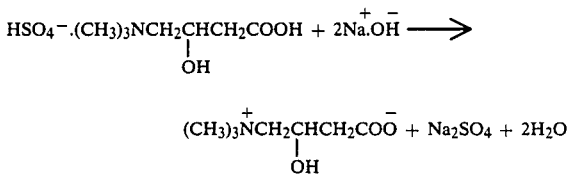

taking by way of example sulphuric acid for the acidication following 1 and caustic soda as the base for the neutralisation.

The solution thus neutralised is treated with a view to replacing its water with a lower alcohol capable of dissolving carnitine. This can be effected as in 2 above, that is by evaporation of the water, preferably under vacuum, and the addition of the alcohol or also by evaporation under a vacuum with entrainment of the alcohol. The new alcoholic solution obtained in this manner is maintained at the temperature at which the carnitine remains dissolved, while the mineral salt (Na sulphate in the above example) formed by reason of the neutralisation, precipitates. A very pure alcoholic solution of carnitine is thus obtained.

5—RECOVERY IN THE DRY STATE

From the alcoholic solution remaining after 4, solid dry carnitine can be recovered, by complete evaporation of the solvent. Another means which improves even further the purity consists in precipitating the carnitine by the addition of a non-solvent to its alcoholic solution; thus the addition of an excess of acetone allows the deposition of very pure solid carnitine.

As mentioned above, any sample of carnitine whatever its origin can be purified by the process of the present invention, which is applied particularly well to the media obtained by the bio-conversion of dehydrocarnitine by the asymmetric reduction thereof by means of NADH, with reduction of the $NAD^+$ formed by the formate ion in the presence of dehydrogenase formate (FDH). Yields of L-carnitine and the purification are remarkable when the FDH hydrogenase is obtained from *Candida Bodiini* or *Pichia Pastoris* yeasts.

The latter types of solutions of carnitine are treated in the non-limitative examples which are given below.

EXAMPLE 1

The preparation of L-carnitine is effected by the action of reduced nicotinamide adenine dinucleotide, NADH, on dehydrocarnitine, and reduction of the $NAD^{30}$ formed, by means of the formic group with dehydrogenase formate FDH as catalyst. The scheme of this synthesis is thus U or 60 mg of commercial dehydrogenase formate lyophilisate, FDH, obtained from *Candida bodiini* (EC 1.2.1.2.—marketed by BOEHRINGER MANNHEIM).

The reactor thus supplied with a solution maintained at 4° C. contains crystallised dehydrocarnitine hydrochloride, dissolved at a concentration of 0.8M and thus also containing 0.8M formic acid. The rate of injection was 1.2 ml/h. The temperature in the reactor was regulated to 30° C. and the pH was maintained at 7.0 by the addition of 2N ammonia controlled by a pH regulation system. After 230 h, a final volume of 315 ml was obtained and a concentration of L-Carnitine of 477 mM, corresponding to a yield of 98%. The solution so obtained was subjected to the following purification operations.

This bioconversion medium was acidified to pH 2.0 by concentrated sulphuric acid. The proteins precipitated. After filtration, the filtrate was evaporated under vacuum (70° C./15 mmHg) followed by entrainment of the water with ethanol. The medium was deprived of water and became enriched in ethanol. The L-Carnitine is soluble in ethanol in the hot; the mineral salts are not and they precipitate. After filtration on a fritted glass, an ethanolic solution of L-Carnitine sulphate was recovered which was precipitated with acetone in the cold (volumetric ratio acetone/ethanol=90/10). The L-Carnitine sulphate is dissolved in water and neutralised to pH=7.2 with concentrated caustic soda.

The aqueous solution obtained is evaporated under vacuum with entrainment of the ethanol. The medium deprived of water caused the sodium sulphate to precipitate in the ethanol. After filtration on fritted glass, an ethanolic solution of L-Carnitine was recovered which contained no sulphate ($Ba^{2+}$ test). The solvent was evaporated to obtain a dry product. The latter was dissolved in the minimum of ethanol in the hot (40° C.) and precipitated in the cold with acetone. The overall yield of the purification is 80%. The yield of the entire preparation of pure L-Carnitine is thus $80 \times 98/100 = 78.4\%$.

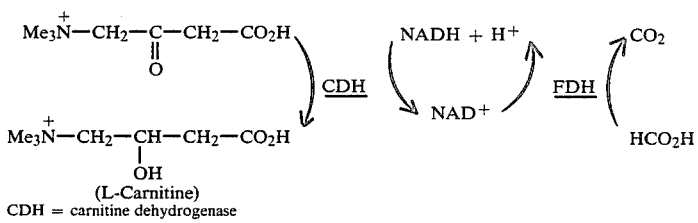

(L-Carnitine)
CDH = carnitine dehydrogenase

The CDH utilised is obtained from an extract of *Pseudomona putida* culture. It was precipitated with ammonium sulphate at 250 g/l from the crude extract (55% of saturation). The residue obtained from 20 ml of the extract was redissolved in 7 ml of $Na_2HPO_4/KH_2PO_4$ 50 mM buffer of pH=7.0, the solution passing on gel filtration (G200), then chromatographed on 5' AMP - Sepharose 4B (enzyme fixed by affinity and then eluated with $NAD^+$ 10 mM) and then passed on to ACA 44 filtration gel, to recover the $NAD^+$ reduced enzyme and the $NaN_3$ (which had been included in the eluation buffers to protect them from contamination).

The pure enzyme so obtained had a specific activity of 55 U/mg; 40 U were then introduced into a 50 ml reactor. This reactor also contained 2 mM of $NAD^+$, 150 mm of $HCO_2NH_4$, 6 mg of chloramphenicol and 40

The characteristics of the product obtained are:
$|\alpha|D^{20} = -30,2°$ (2.5, water).
sulphates < 400 ppm.
$^1H$ RMN ($D_2O$)(300 MHz):δ(ppm): (4.4 (quintuplet; J:5 Hz; 1H); 3.25 (doublet) J:5 Hz; 2H); 3.05 (singulet, 9H); 2.25 (doublet of doublet; 2H).
Enzymatic measurement: 100% L-carnitine.

EXAMPLE 2

(comparative)

All the operations of example 1 are repeated, with the sole difference that the FDH employed was derived from *Torulopsis candida* yeast (GFP 206), as described in example 5 page 8 of French Pat. No. 2398046. The yield in purified L-Carnitine was thus only 58% and the purity of the final product was only 92%. This shows the interest of FDH derived from *Candida Bodiini*, corresponding to the preferred form of the present invention.

EXAMPLE 3

Seeking to limit the increase in the volume during the bioconversion, use was made of reactants in more concentrated solutions of dehydrocarnitine, formic acid and ammonia, an on the other hand the concentration in $NAD^+$ was reduced.

Thus into the 50 ml reactor, a solution containing the following was introduced $Na_2HO_4/KH_2PO_4$ 50 mM pH: 7.5
$NAD^+$ 0.2 mM
6 mg chloramphenicol
40 U of CDH summarily purified as described below
25 U of BOEHRINGER-MANNHEIM FDH derived from *Candida bodiini*.

The CDH extracted from *P. Putida* had been precipitated with ammonium sulphate (55% of saturation), centrifuged and the residue was redissolved in the 50 mM phosphate buffer of pH 7.5; the solution obtained was dialysed for 16 h against the same buffer.

The reactor was supplied with a solution maintained at 4° C., containing dehydrocarnitine and formic acid at the concentration of 1.6M for each. The rate was 0.6 ml/h. The temperature of the reactor was maintained at 30° C. and the pH at 7.5 by the controlled addition of 8N ammonia. After 48 hours, a final volume of 90 ml was obtained and a concentration of L-Carnitine of 500 mM or a yield of 98%.

Purification effected as in example 1 gave the same result.

EXAMPLE 4

The same test as in Example 3 was carried out with FDH from *Pichia Pastoris* with the following modifications:

$NAD^+$ 0.4 mM
$HCO_2NH_4$ 500 mM
in the absence of chloramphenicol which had been omitted because the strong salinity due to the initial high concentration of ammonium formate limited any risk of contamination. FDH extracted from a culture of *Pichia Pastoris* precipitated with ammonium sulphate (50% of saturation), was centrifuged and the residue was redissolved in a 50 mM phosphate buffer at pH 7.5, the solution obtained being dialysed for 16 h against this buffer. The other parameters of the reactor were those of example 3.

After 49 h, the final volume was 60 ml and the concentration of L-Carnitine was 70 mM, which corresponded to a yield of 93%.

Measurement of the enzymes showed a residual activity of 90% in CDH and 90% in FDH.

Purification of the L-Carnitine obtained, effected in the manner of Example 1 gave the same results; it thus appeared that the FDH from *Pichia pastoris* gives equivalent results to those of FDH from *Candida bodiini*, even better results being obtained with FDH from *Torulopsis candida* (example 2)

We claim:
1. A method of purifying fermentation produced carnitine from an aqueous solution containing the carnitine and also containing proteins, which method comprises the steps of:
  (a) acidifying the aqueous solution, whereby protenaceous material in the aqueous solution precipitates;
  (b) separating any protein precipitate so formed from the aqueous solution;
  (c) replacing the water of the aqueous solution with a lower alcohol under conditions such that the carnitine in the aqueous solution dissolves in the lower alcohol while mineral salts which were dissolved in the aqueous solution precipitate; and
  (d) separating the mineral salt precipitate from the purified solution of carnitine in the lower alcohol.
2. A method according to claim 1 in which the acidification is effected to a pH of about 1 to 3.
3. A method according to claim 2 in which the acidification is effected employing sulfuric, phosphoric, perchloric or benzene-sulfonic acid.
4. A method according to claim 3 in which the lower alcohol is methanol, ethanol, n-propanol, isopropanol, n-butanol, isobutanol, t-butanol or a mixture thereof.
5. A method according to claim 4 in which the aqueous solution is acidified with sulfuric acid to a pH of about 2 and the water is in the aqueous solution is replaced with ethanol.
6. A method according to claim 1 in which the lower alcohol is at a temperature from 20° to 100° C. sufficient to completely dissolve the carnitine.
7. A method according to claim 1 in which the alcohol in the purified solution of carnitine in the lower alcohol is evaporated and the resulting salt of the carnitine and the acid used in the acidifying step is dissolved in water.
8. A method according to claim 7 wherein the aqueous solution of the carnitine salt is neutralized to a pH of 6.9 to 7.4 whereby an aqueous solution of amphoteric carnitine is realized.
9. A method according to claim 8 wherein the water of the aqueous solution of amphoteric carnitine is removed and replaced with a lower alcohol under conditions such that the amphoteric carnitine dissolved in the alcohol and salts resulting from the neutralization of the aqueous solution precipitate and in which the salt precipitate is removed.
10. A method according to claim 1 in which a ketone is added to the purified solution of carnitine in lower alcohol to precipitate a salt of carnitine and the acid used in the acidification step and the salt so precipitated is dissolved in water.
11. A method according to claim 10 in the aqueous solution of precipitated salt is neutralized to a pH of 6.9 to 7.4 whereby the salt of carnitine is converted into amphoteric carnitine.
12. A method according to claim 11 in which the water of the aqueous solution of amphoteric carnitine is removed and replaced with a lower alcohol under conditions such that the carnitine dissolves in the alcohol while salt resulting from the neutralization of the aqueous solution precipitate and is separated from the solution of amphoteric carnitine.

* * * * *